United States Patent
Kota et al.

(10) Patent No.: US 9,823,174 B2
(45) Date of Patent: Nov. 21, 2017

(54) DEVICES AND METHODS FOR SORTING DROPLETS BY SURFACE TENSION

(71) Applicant: Colorado State University Research Foundation, Fort Collins, CO (US)

(72) Inventors: Arun K. Kota, Fort Collins, CO (US); Sanli Movafaghi, Fort Collins, CO (US); Shantanu Jathar, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/443,620

(22) Filed: Feb. 27, 2017

(65) Prior Publication Data

US 2017/0176311 A1    Jun. 22, 2017

Related U.S. Application Data

(63) Continuation of application No. PCT/US2016/062903, filed on Nov. 18, 2016.

(60) Provisional application No. 62/257,349, filed on Nov. 19, 2015.

(51) Int. Cl.
    *G01N 13/02*    (2006.01)
    *G01N 33/22*    (2006.01)
    *G01N 21/33*    (2006.01)

(52) U.S. Cl.
    CPC ............. *G01N 13/02* (2013.01); *G01N 21/33* (2013.01); *G01N 33/22* (2013.01)

(58) Field of Classification Search
    CPC ......... G01N 31/02; G01N 33/22; G01N 21/33
    See application file for complete search history.

(56) References Cited

U.S. PATENT DOCUMENTS

| | | | |
|---|---|---|---|
| 3,415,109 A | 12/1968 | Sucker et al. | |
| 7,025,836 B1 | 4/2006 | Zimmer et al. | |
| 8,081,308 B2* | 12/2011 | Wang | G01J 3/02 356/300 |
| 8,574,704 B2* | 11/2013 | Smith | B08B 17/065 428/141 |
| 9,181,455 B2* | 11/2015 | Liang | C03C 17/30 |
| 2010/0114514 A1* | 5/2010 | Wang | G01J 3/02 702/82 |

(Continued)

FOREIGN PATENT DOCUMENTS

CN    103884755 A    6/2014

OTHER PUBLICATIONS

Thampi et al. "Do liquid drops roll or slide on inclined surfces?", May 2014.*

(Continued)

*Primary Examiner* — John Fitzgerald
(74) *Attorney, Agent, or Firm* — Michael H. Haukaas; Haukaas Fortius PLLC

(57) ABSTRACT

A tunable superomniphobic surface with flower-like $TiO_2$ nanostructures was fabricated into a device with precisely tailored surface energy domains that can sort droplets by surface tension. This apparatus and method for droplet sorting will enable inexpensive and energy-efficient analytical devices for personalized point-of-care diagnostic platforms, lab-on-a-chip systems, fuel sensor applications, biochemical assays and biosensors.

29 Claims, 11 Drawing Sheets

(56) References Cited

U.S. PATENT DOCUMENTS

| | | | | |
|---|---|---|---|---|
| 2013/0309450 | A1* | 11/2013 | Khine | B08B 17/065 |
| | | | | 428/141 |
| 2014/0011013 | A1 | 1/2014 | Jin et al. | |
| 2014/0023852 | A1 | 1/2014 | Bower et al. | |
| 2016/0153094 | A1* | 6/2016 | Tuteja | C23F 1/16 |
| | | | | 216/53 |
| 2016/0251803 | A1* | 9/2016 | Tuteja | D21H 17/11 |
| 2017/0022372 | A1* | 1/2017 | Lynn | C09D 5/1681 |

OTHER PUBLICATIONS

Chu, et al., "Superamphiphobic Surfaces," Chem. Soc. Rev., 43:2784-2798, Jan. 2014.

International Search Report and Written Opinion of the ISA/US in Int'l Application No. PCT/US2016/062903, dated Jan. 31, 2017, 7pgs.

Kota, et al., "Hierarchically Structured Superoleophobic Surfaces with Ultralow Contact Angle Hysteresis," Adv. Mater., 24:5838-5843, Aug. 2012.

Kota, et al., "Superomniphobic Surfaces: Design and Durability," MRS Bulletin, 38(5):383-390, May 2013.

Kota, et al., "The Design and Applications of Superomniphobic Surfaces," NPG Asia Materials, pp. 1-16, Jul. 2014.

Liao, et al., "Liquid Droplet Movement on Horizontal Surface with Gradient Surface Energy," Sci. in China Series E: Technological Sciences, 49(6):733-741, Jan. 2006.

Liu, et al., "Turning a Surface Superrepellent Even to Completely Wetting Liquids," Science, 342(6213):1096-1100, No. 2014.

Movafaghi, et al., "Tunable Superomniphobic Surfaces for Sorting Droplets by Surface Tension," Lab Chip, 16:3204-3209, Jul. 2016.

Wen, et al., Bioinspired Super-Wettability from Fundamental Research to Practical Applications, Angew Chem Int Ed Engl., 54(11):3387-3399, Mar. 2015.

\* cited by examiner

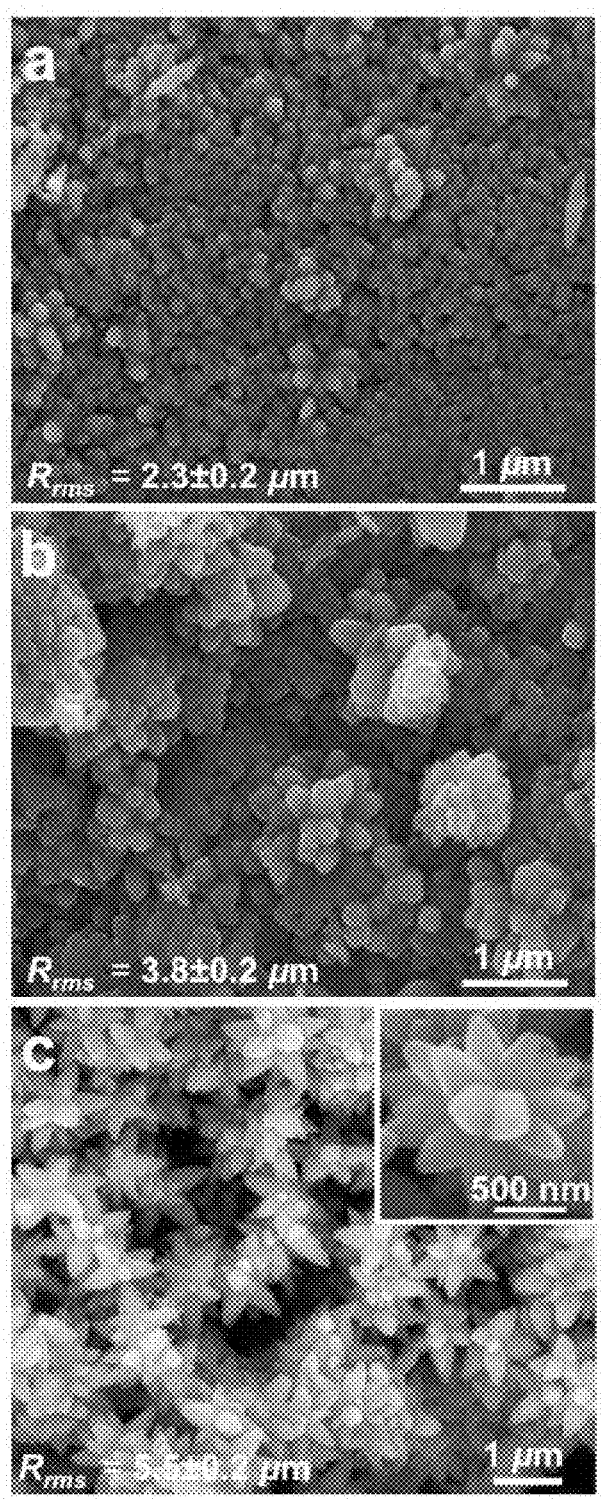
Fig. 1a-f

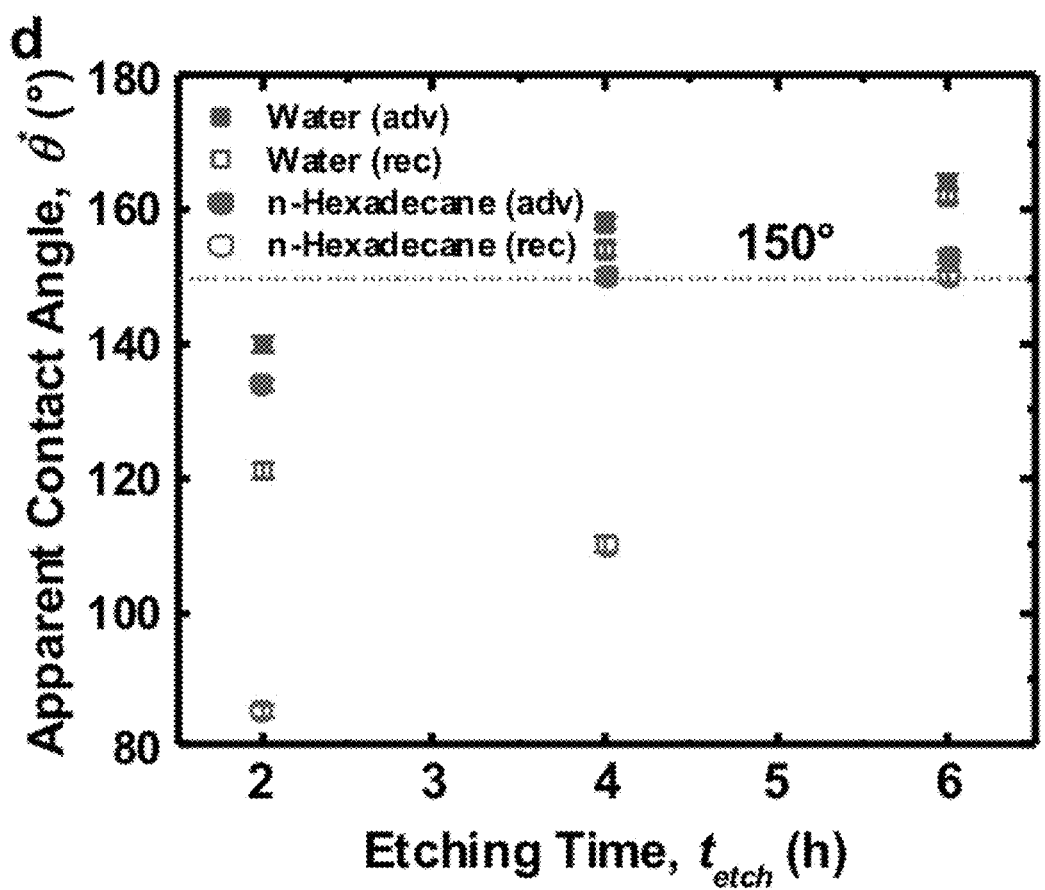
*Fig. 1a-f (cont.)*

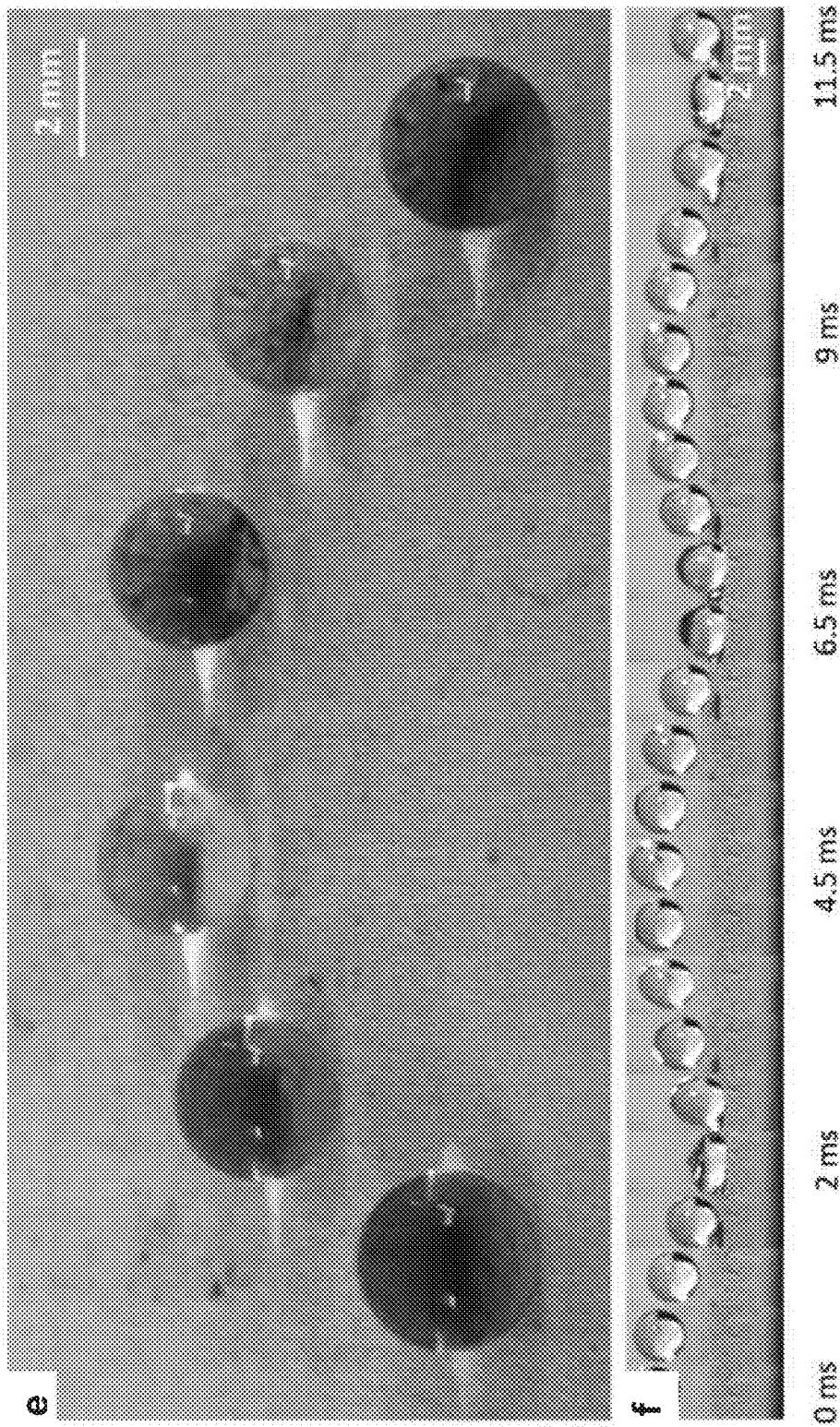
Fig. 1a-f (cont.)

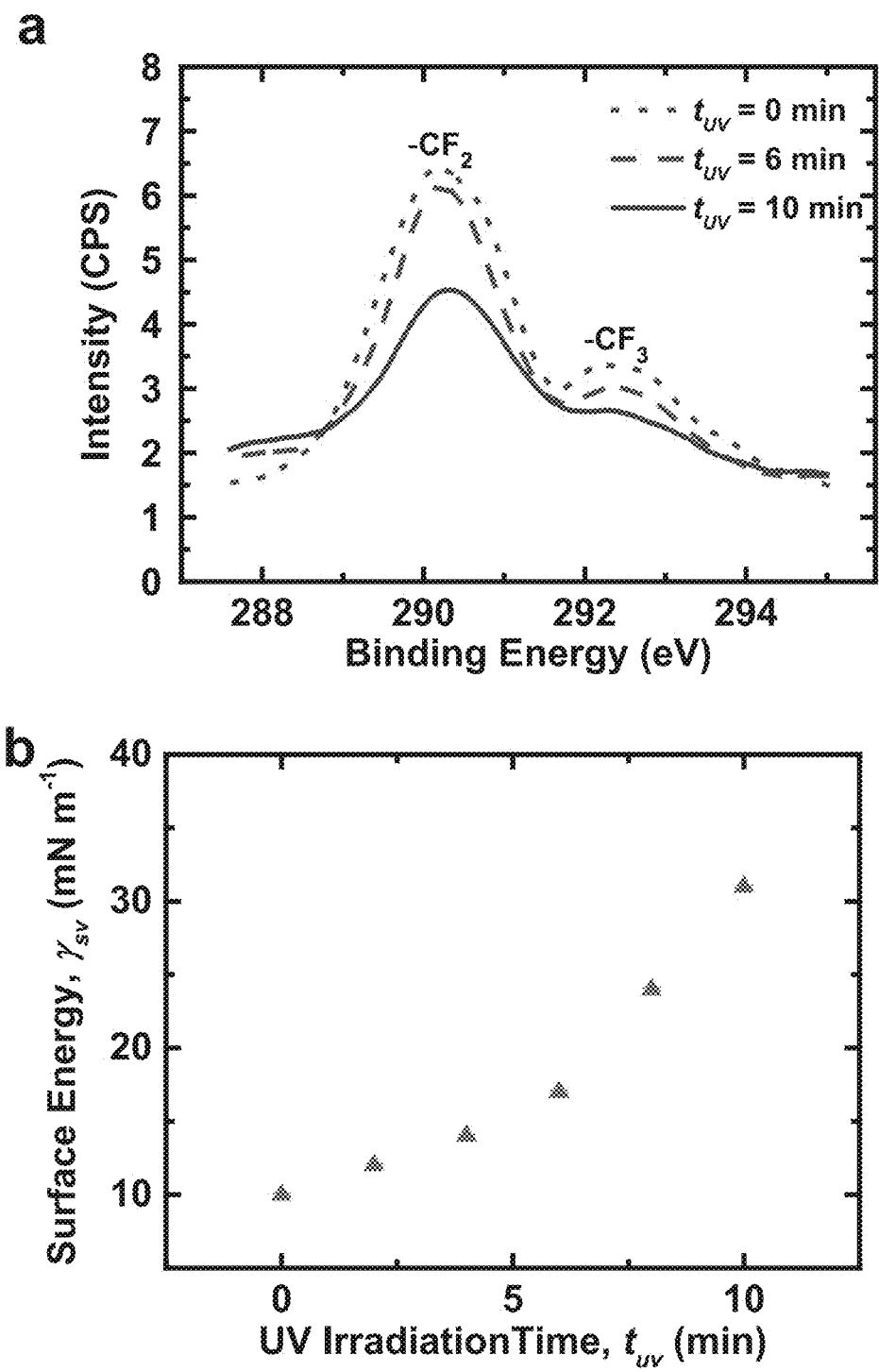
Fig. 2a-b

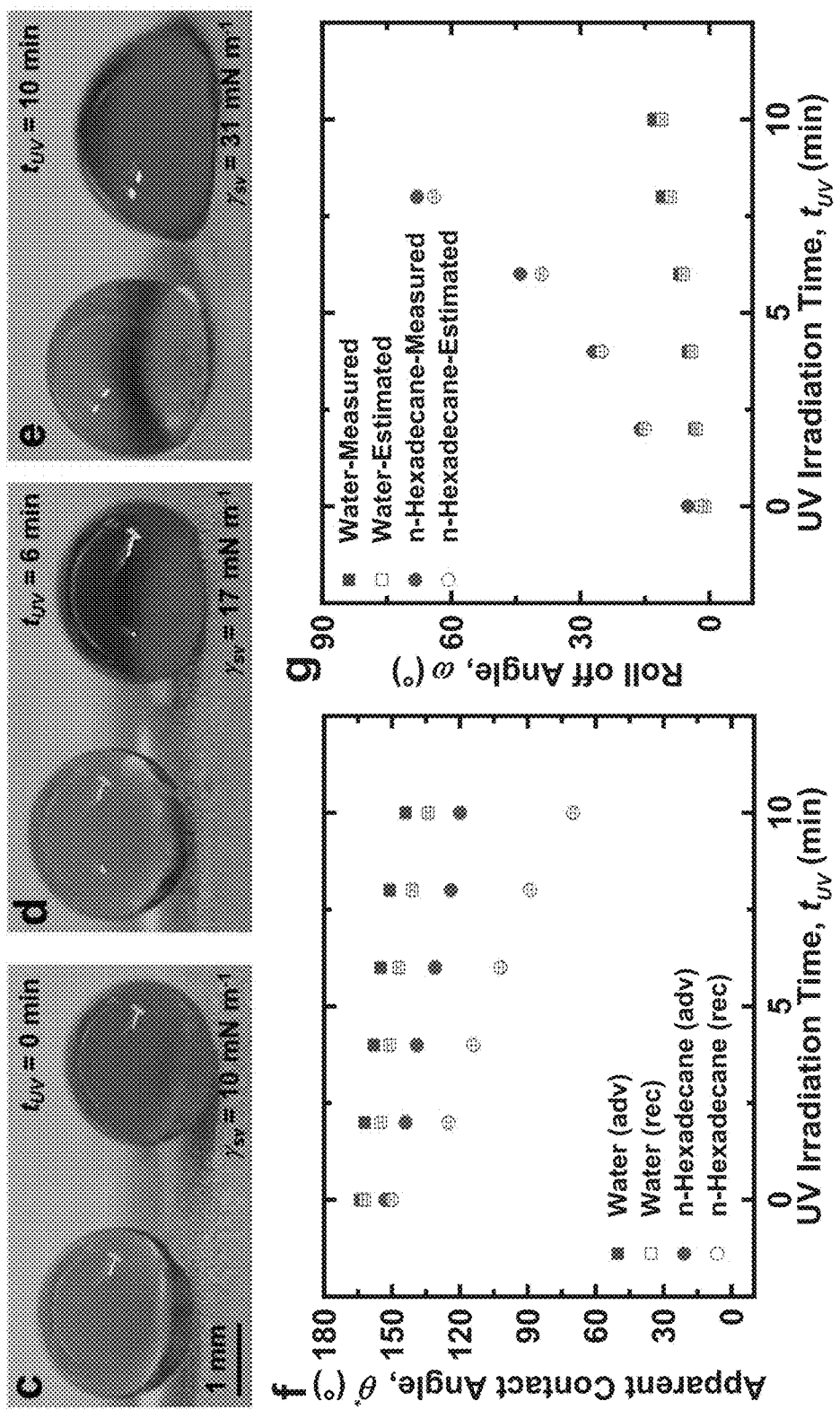
Fig. 2c-g

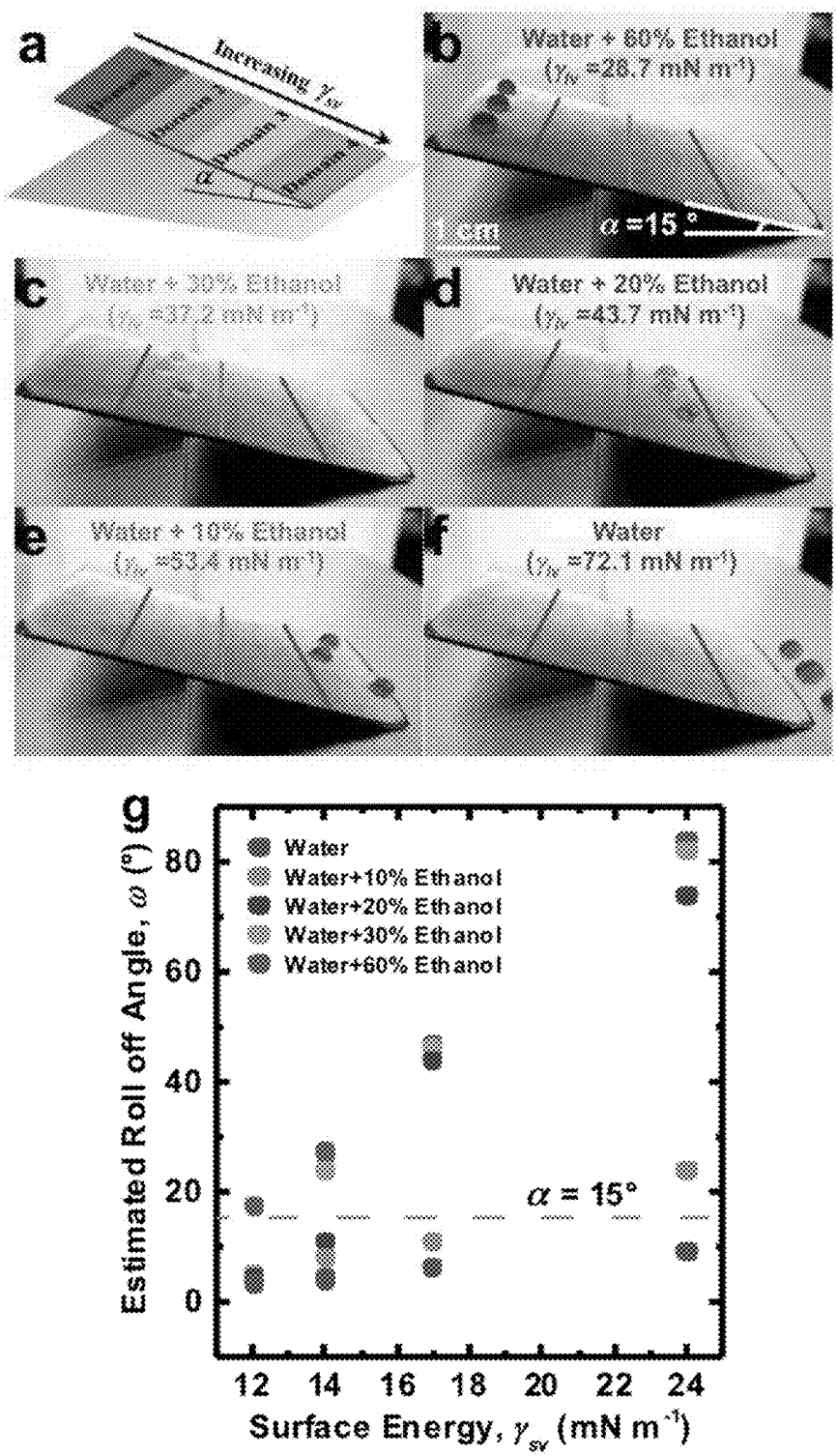
*Fig. 3a-g*

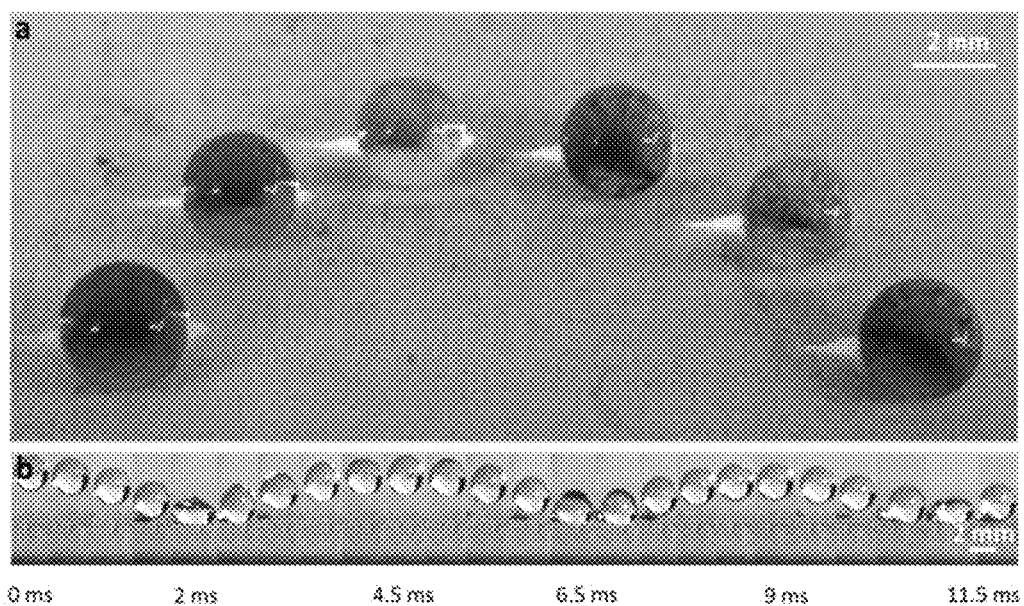
*Fig. 7a-b*

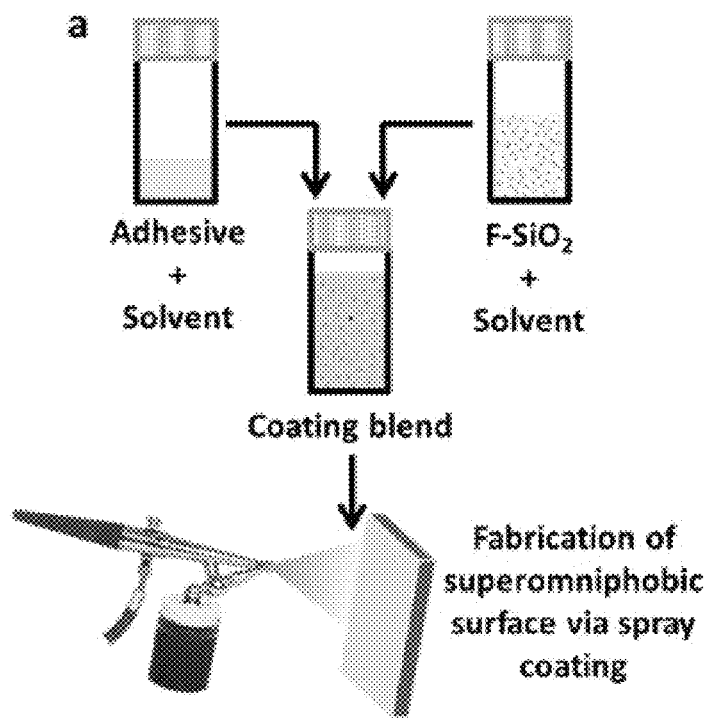
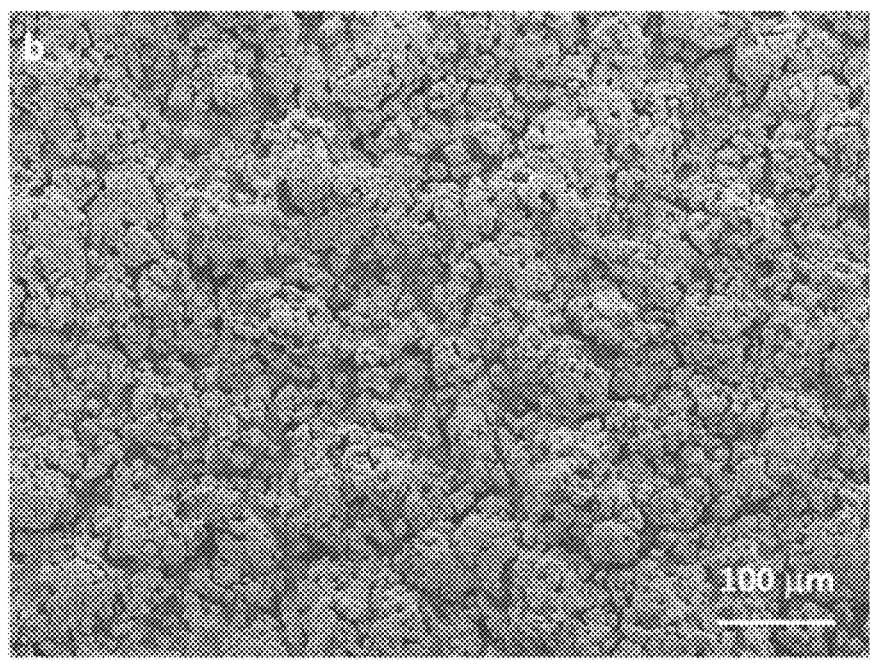
Fig. 8a-b

DEVICES AND METHODS FOR SORTING DROPLETS BY SURFACE TENSION

RELATED APPLICATIONS

This application is a continuation under 35 U.S.C. 111(a) of International Application No. PCT/US2016/062903 filed Nov. 18, 2016, which application claims priority under 35 U.S.C. §119(e) to U.S. Provisional Patent Application No. 62/257,349 filed Nov. 19, 2015, which applications are incorporated herein by reference.

BACKGROUND OF THE INVENTION

Recent years have witnessed a significant spike in manipulation of liquid droplets because of their applications in microfluidic diagnostics, DNA analysis, drug discovery, microreactors and biosensing. Particularly, droplet manipulation on super-repellent surfaces (i.e., surfaces that are extremely repellent to liquids) has been widely studied because droplets exhibit high mobility, minimal contamination and minimal sample loss on super-repellent surfaces. Various droplet manipulation methods including electric fields, magnetic fields, guiding tracks, and wettability gradients, have been developed to enable the transportation, trapping, merging and splitting of droplets on super-repellent surfaces. However, there are very few studies that demonstrate droplet sorting (i.e., systematically ordering or categorizing droplets by a physical property of the droplet) on super-repellent surfaces.

Accordingly, there is a need for inexpensive and energy-efficient analytical devices for personalized point-of-care diagnostic platforms, lab-on-a-chip systems, biochemical assays and biosensors. This problem is solved by utilizing tunable superomniphobic surfaces with flower-like $TiO_2$ nanostructures to fabricate a simple device with precisely tailored surface energy domains that, for the first time, can sort droplets by surface tension. We envision that our methodology for droplet sorting will enable inexpensive and energy-efficient analytical devices that can conveniently perform diagnostic tests and provide quick results.

SUMMARY

This disclosure provides a synthesized tunable superomniphobic surface with fluorinated, flower-like $TiO_2$ nanostructures. We demonstrate that the surface chemistry, and consequently the solid surface energy and contact angle hysteresis (i.e., the difference between the advancing [maximum] and receding [minimum] contact angles), of our superomniphobic surfaces can be tuned using UV irradiation. This allows us to systematically tune the mobility of droplets with different surface tensions on our superomniphobic surfaces. Each of these surfaces with same surface texture, but different solid surface energy allows certain high surface tension liquid droplets to freely roll past the surface while "trapping" other low surface tension liquid droplets due to adhesion. Leveraging this selective mobility of droplets based on their surface tension, we fabricated a simple device with precisely tailored discrete surface energy domains that, for the first time, can sort droplets by their surface tension. The novelty of our work lies in the design of discrete and tunable superomniphobic domains as well as the ability of the device to sort droplets by surface tension.

Accordingly, this disclosure provides an apparatus for analyzing a property of a liquid, the apparatus comprising: a surface comprising superomniphobic and omniphobic areas, the surface having a first end and a distal end, and a gradient of two or more domains, each domain occupying different positions on the surface, wherein a first domain is at the first end and each other domain has an increased surface energy relative to the domain immediately preceding it; and wherein when a liquid droplet is placed on the first domain, having the lowest surface energy, and the surface is inclined relative to horizontal, the droplet traverses part or all of one or more of the domains and the domain where the droplet comes to the rest is indicative of the surface tension of the liquid.

In another embodiment of the apparatus, the apparatus comprises: a titanium metal sheet having a first end and a distal end, and a layer of a $TiO_2$ nano-flower three-dimensional structure having a re-entrant surface texture wherein the $TiO_2$ is surface modified with a fluoroalkyl silane and the surface modified $TiO_2$ nano-flower structures form a superomniphobic surface on the sheet; and the surface comprises a gradient of two or more domains from the first end to the distal end;

wherein the domains occupy different positions on the sheet and are ordered in increasing surface energy, the first end of the sheet having the lowest surface energy, the distal end of the sheet having the highest surface energy, and each of the second or more domains have increased surface energy relative to the domain immediately preceding it; the first domain comprises the superomniphobic surface and each of the second or more domains comprise omniphobic areas having less than superomiphobicity; and the width of each domain is about 0.1 cm to about 10 cm.

This disclosure also provides a method for analyzing a property of a liquid, the method comprising:

a) placing a liquid droplet on an apparatus comprising:
   i) a surface comprising superomniphobic and omniphobic areas, the surface having a first end and a distal end, the first end at the top of an incline and having a slope toward the distal end; and
   ii) the surface comprises a gradient of two or more domains, each domain occupying different positions on the surface, wherein the first domain, having the lowest surface energy, is closest to the first end and each of the second or more domains have an increased surface energy relative to the domain immediately preceding it;
wherein when the droplet is placed at the first end, the droplet traverses part or all of one or more of the domains; and b) determining the final position of the droplet;
wherein the domain where the droplet comes to the rest is indicative of the surface tension of the liquid.

Additionally, this disclosure provides a method for analyzing a property of a liquid, the method comprising:

a) placing one or more liquid droplets on an apparatus comprising:
   one or more individual surfaces comprising superomniphobic and omniphobic areas, each surface having a first end and a distal end, the first end of each individual surface at the top of an incline and having a slope toward the distal end;
   wherein each of two or more individual surfaces have a different surface energy and a different tilt angle, or each of two or more individual surfaces have about the same surface energy and a different tilt angle,
   wherein
      when the droplet is placed at the first end of a surface, the droplet traverses part or all of one or more of the domains of the surface; or when the droplet is placed at the first end of a surface, the droplet traverses part or all of one individual surface having a fixed surface energy wherein the tilt angle is changed after each individual droplet is placed at the first end and traverses part or all of one individual surface; and b) determining the final position of the droplet;

wherein the domain where the droplet comes to the rest is indicative of the surface tension of the liquid.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1a-f. a), b) and c) Scanning electron microscope (SEM) images showing the morphology of $TiO_2$ nanostructures after 2, 4 and 6 hours, respectively, of etching under hydrothermal conditions. The root mean square roughness $R_{rms}$ increased with etching time. The inset in (c) shows the re-entrant texture of the flower-like $TiO_2$ nanostructure. d) Apparent contact angles of water and n-hexadecane on the surfaces shown in (a)-(c) after the surfaces are fluorinated. e) Droplets (left to right) of n-hexadecane, water+60% ethanol, water+30% ethanol, water+20% ethanol, water+10% ethanol, and water showing very high apparent contact angles on the superomniphobic $TiO_2$ surface. f) A series of snapshots showing a droplet of water+60% ethanol bouncing on the superomniphobic $TiO_2$ surface.

FIG. 2a-g. a) High resolution C1s X-ray photo-electron spectroscopy (XPS) scan showing the degradation of $—CF_2$ and $—CF_3$ groups with increasing UV irradiation time $t_{UV}$. b) The solid surface energy of fluorinated $TiO_2$ surfaces increasing with increasing UV irradiation time. c), d) and e) The wettability of water (blue; droplet on left) and n-hexadecane (red; droplet on right) droplets on fluorinated $TiO_2$ surfaces increasing with increasing UV irradiation time. f) Apparent contact angles of water and n-hexadecane on fluorinated $TiO_2$ surfaces decreasing with increasing UV irradiation time. g) The measured roll off angles of ~5 μL n-hexadecane droplets on fluorinated $TiO_2$ surfaces increasing more rapidly compared to those of ~5 μL water droplets with increasing UV irradiation time. The measured roll off angles are in good agreement with the estimated roll off angles.

FIG. 3a-g. a) Schematic of a device with multiple, discrete domains of identical texture, but different solid surface energies. b)-f) A series of snapshots showing the sorting of ~5 μL liquid droplets with different surface tension values using a device with four discrete surface energy domains tilted at an angle of 15° relative to the horizontal. Each domain is 15 mm±2 mm long. g) The estimated roll off angles of 5 μL liquid droplets with different surface tension values on super-repellent surfaces with different solid surface energies.

FIG. 7a-b. a) Droplets (left to right) of n-hexadecane, water+60% ethanol, water+30% ethanol, water+20% ethanol, water+10% ethanol, and water showing very high apparent contact angles on a superomniphobic surface. b) A series of snapshots showing a droplet of water+60% ethanol bouncing on a superomniphobic surface.

FIG. 8a-b. a) Schematic depicting the fabrication of superomniphobic surfaces. b) The SEM image showing superomniphobic surface texture.

DETAILED DESCRIPTION

Figure 4:
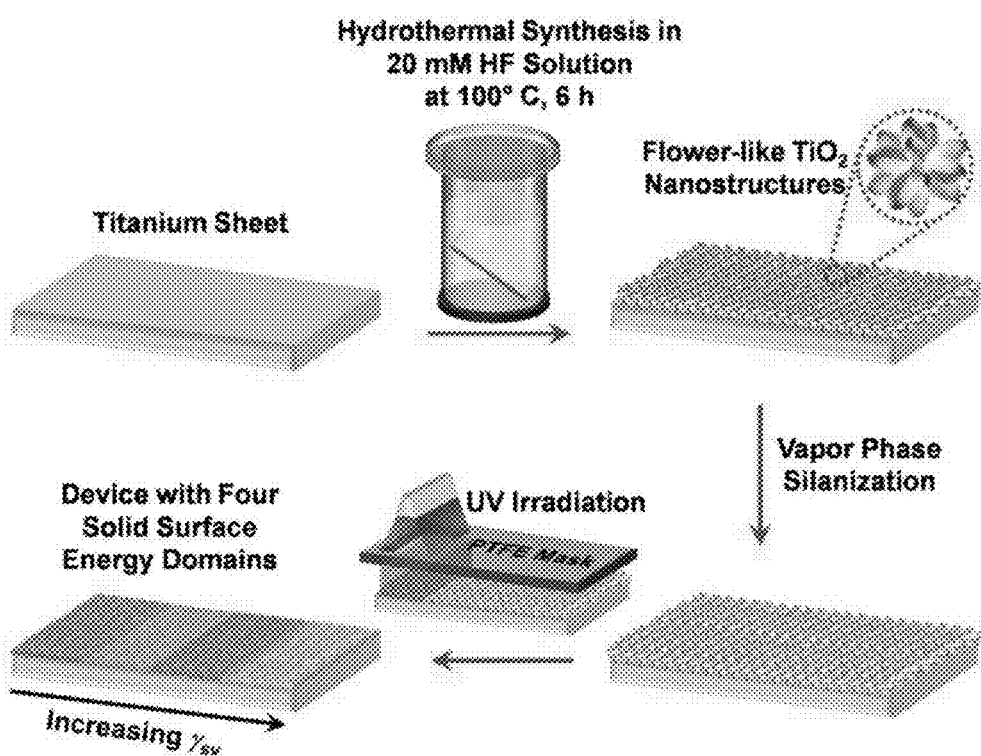
FIG. 4. Schematic depicting the fabrication of a device with discrete solid surface energy domains.

Droplet sorting occurs on our device due to a balance between the work done by gravity and the work expended due to adhesion (that depends on liquid surface tension), without the need for any external energy input. Our devices can be fabricated easily in a short time and we demonstrate that each device can be reused multiple times (more than about 25 times in our experiments) to sort droplets by surface tension over a wide range (28.7 mN/m to 72.1 mN/m). Further, our devices can be readily used to estimate the surface tension of miscible liquid mixtures that in turn enables the estimation of mixture composition. This is particularly useful for in-the-field and on-the-go operations, where complex analysis equipment is unavailable. We envision that our methodology for droplet sorting will enable inexpensive and energy-efficient analytical devices for personalized point-of-care diagnostic platforms, lab-on-a-chip systems, biochemical assays and biosensors.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more domains on a surface refers to one to five, or one to ten, for example, if the surface has multiple domains.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified.

Embodiments of the Invention

Various embodiments of the invention also include an apparatus for analyzing a property of a liquid, the apparatus comprising:

a surface comprising superomniphobic and omniphobic areas, the surface having a first end and a distal end, and a gradient of two or more domains, each domain occupying different positions on the surface, wherein a first domain is at the first end and each other domain has an increased surface energy relative to the domain immediately preceding it; and wherein when a liquid droplet is placed on the first domain, having the lowest surface energy, and the surface is inclined relative to horizontal, the droplet traverses part or all of one or more of the domains and the domain where the droplet comes to the rest is indicative of the surface tension of the liquid.

In one embodiment, the superomniphobic and omniphobic areas comprise $TiO_2$ nano-flower three-dimensional structures that establish a re-entrant texture on the surface. In another embodiment, the $TiO_2$ structures are surface modified with a fluoroalkyl silane, a perfluoroalkyl silane, 1H, 1H,2H,2H-perfluorooctylphosphate (PFOP), 1H,1H, 2H,2H-perfluorooctanoic acid (PFOA), 1H,1H,2H,2H-perfluorooctyl trichlorosilane (PFOTS), 1H,1H,2H,2H-perfluorodecyl trichlorosilane (PFDTS), 1H,1H,2H,2H-perfluorodecane-1-thiol (PFDSH), 1H,1H,2H,2H-perfluorodecyl acrylate (PFDAE), perfluorooctyl trichlorosilane, a perfluorodecyl polyhedral oligomeric silsesquioxane (FluoroPOSS), perfluorinated phosphates, fluorinated thiols, fluorinated acids, fluorinated monomers, fluorinated polymers, or fluorinated copolymers.

In one embodiment, the first end is at the top of an incline having a slope toward the distal end. In another embodiment, the longitudinal width of each domain is about 0.5 mm to about 10 cm, or the longitudinal width of each domain is about 0.5 cm to about 2 cm. The longitudinal width can also be about 0.1 mm to about 500 mm, about 2 cm to about 8 cm, about 5 cm to about 20 cm, about 20 cm to about 100 cm.

In another embodiment, a titanium metal sheet having a first end and a distal end, and a layer of a $TiO_2$ nano-flower three-dimensional structure having a re-entrant surface texture wherein the $TiO_2$ is surface modified with a fluoroalkyl silane and the surface modified $TiO_2$ nano-flower structures form a superomniphobic surface on the sheet; and the surface comprises a gradient of two or more domains from the first end to the distal end; wherein the domains occupy different positions on the sheet and are ordered in increasing surface energy, the first end of the sheet having the lowest surface energy, the distal end of the sheet having the highest surface energy, and each of the second or more domains have increased surface energy relative to the domain immediately preceding it; the first domain comprises the superomniphobic surface and each of the second or more domains comprise omniphobic areas having less than superomniphobicity; and the width of each domain is about 0.1 cm to about 10 cm.

In other embodiments, a liquid droplet is placed at the first end closest to the lowest surface energy domain of the gradient and the surface is inclined relative to horizontal, the droplet traverses part or all of one or more of the domains and the domain where the droplet comes to the rest is indicative of the surface tension of the liquid.

In some embodiments, superomniphobic surfaces can be created by a variety of techniques, including but not limited to, spray coating, photolithography, or hydrothermal synthesis.

In various embodiments, the difference in surface energy between each adjacent domain is less than about 20 mN/m, and the difference in surface energy between at least two or more adjacent domains is less than 10 mN/m. The difference in surface energy between at least two or more adjacent domains can also be less than 50, mN/m, 30 mN/m, 5 mN/m, or 1 mN/m.

In one embodiment of a method for analyzing a property of a liquid, the method comprises:
a) placing a liquid droplet on an apparatus comprising:
i) a surface comprising superomniphobic and omniphobic areas, the surface having a first end and a distal end, the first end at the top of an incline and having a slope toward the distal end; and
ii) the surface comprises a gradient of two or more domains, each domain occupying different positions on the surface, wherein the first domain, having the lowest surface energy, is closest to the first end and each of the second or more domains have an increased surface energy relative to the domain immediately preceding it;
wherein when the droplet is placed at the first end, the droplet traverses part or all of one or more of the domains; and
b) determining the final position of the droplet;
wherein the domain where the droplet comes to the rest is indicative of the surface tension of the liquid.

In various embodiments, if the roll off angle of the droplet is lower than the tilt angle of the incline of a particular domain, the droplet rolls off the domain, and if the roll off angle is higher than the tilt angle of the incline of a particular domain, the droplet remains on the domain.

In additional embodiments, the superomniphobic and omniphobic areas comprise $TiO_2$ nano-flower three-dimensional structures that establish a re-entrant texture on the surface, wherein the $TiO_2$ structures are surface modified with a fluoroalkyl silane or a perfluoroalkyl silane.

In various embodiments, the second or more domains surfaces have been modified with, for example, ultraviolet irradiation, plasma, or chemicals, to increase the surface energy of the domains, wherein increasing the surface modification provides a domain having increased surface energy.

In other embodiments, the surface energy of each one of the domains has been tuned by irradiating the domain with a 254 nm ultraviolet lamp wherein the distance between the ultraviolet lamp and the domain is about 2 cm and the irradiation time is from 10 seconds to 60 minutes, or the irradiation is carried out for 10 seconds to 10 minutes. The distance between the ultraviolet lamp and the domain can also range from about 0.1 cm to about 10 cm. The irradiation time can also be about 1 second to about 5 minutes. Furthermore, the wattage from the ultraviolet lamp can range from about 1 watt to about 200 watts.

In additional embodiments, the difference in surface energy between each adjacent domain is less than about 20 mN/m, the difference in surface energy between two or more adjacent domains is less than 10 mN/m, or the difference in surface energy between two or more adjacent domains is less than about 3 mN/m.

In other embodiments, the incline has a tilt angle of about 0.5° to about 75°, relative to horizontal, the tilt angle is about 10° to about 45°, or the tilt angle is about 15°.

In one embodiment, the volume of the droplet is about 0.1 µL to about 200 µL, or the volume of the droplet is about 1 µL to about 10 µL. In additional embodiments, the diameter of the droplet is about 0.1 mm to about 4 mm, or about 0.5 mm to about 2 mm.

In other embodiments, the liquid is a pure compound or the liquid comprises a mixture of two or more components, wherein liquids of different compositions achieve different final positions, thereby indicating their different compositions relative to each other. In additional embodiments, the droplet comprises aqueous ethanol, a fuel mixture, a mixture of gasoline and kerosene, a mixture of diesel and kerosene, diesel, gasoline, biofluids, blood, or urine.

In various embodiments, the method is carried out with two or more droplets, optionally with different compositions, the method further comprising sorting each droplet by its final position where the final position is indicative of each droplet's composition or indicative of each droplet's surface tension.

In various embodiments, the surface tension of droplets that can be sorted have surface tensions in the range of about 20 mN/m to about 80 mN/m. In other embodiments, the surface tension of droplets can be lower than about 30 mN/m. In further embodiments, the surface tension of droplets can be higher than about 70 mN/m.

In one embodiment, the apparatus comprises two or more surfaces at different angles. In other embodiments, the apparatus comprises two to about 100 domains, about 5 domains to about 50 domains, about 10 domains to about 1000 domains, or more than about 500 domains.

In various embodiments of a method for analyzing a property of a liquid, the method comprises:

a) placing one or more liquid droplets on an apparatus comprising:

one or more individual surfaces comprising superomniphobic and omniphobic areas, each surface having a first end and a distal end, the first end of each individual surface at the top of an incline and having a slope toward the distal end;

wherein each of two or more individual surfaces have a different surface energy and a different tilt angle, or each of two or more individual surfaces have about the same surface energy and a different tilt angle, wherein when the droplet is placed at the first end of a surface, the droplet traverses part or all of one or more of the domains of the surface; or when the droplet is placed at the first end of a surface, the droplet traverses part or all of one individual surface having a fixed surface energy wherein the tilt angle is changed after each individual droplet is placed at the first end and traverses part or all of one individual surface; and b) determining the final position of the droplet;

wherein the domain where the droplet comes to the rest is indicative of the surface tension of the liquid.

In additional embodiments, the surface energy of one or more of each individual surface has been tuned by irradiating at ultraviolet wavelengths for about 10 seconds to about 60 minutes, wherein the ultraviolet wavelength is near ultraviolet, middle ultraviolet, or far ultraviolet. The ultraviolet wavelength can also range from about 10 nm to about 400 nm.

In various embodiments, the final position of each droplet is indicative of the droplet's composition or indicative of the droplet's surface tension.

In other embodiments, the droplet comprises aqueous ethanol, a hydrocarbon fuel, or a biofluid. In further embodiments, the droplet comprises gasoline, diesel fuel, biodiesel, kerosene, aviation fuel, methanol, or a combination thereof. In additional embodiments, the droplet comprises a mixture of gasoline and kerosene, or a mixture of diesel and kerosene. Other embodiments of the biofluid include blood, blood plasma, blood serum, urine, or saliva.

Liquid repellent surfaces in this disclosure have been modified to comprise a hierarchy of microstructures and nanostructures of, for example, but not limited to, clusters of substantially petal-like geometries arranged in a flower-like three-dimensional configuration and/or a re-entrant configuration such as the morphology shown in FIG. 1c. The nano-flower structure is illustrated as an example, whereas the nanostructure can also comprise different geometries and different configurations exhibiting liquid repellent properties on a surface. Additionally, the three-dimensional structures can form a single layer of clusters on the surface or multiple layers of clusters on the surface and clustering can be evenly distributed on the surface or unevenly distributed on the surface, thereby creating different textures on the surface. Furthermore, the liquid repellent surfaces may be crystalline in structure or amorphous in structure, or a combination thereof.

Liquid repellent properties of surfaces can be further enhanced by contacting or treating the surface with one or more reagents comprising, but not limited to, fluorine or fluorinated hydrocarbons. In this disclosure, the nano-flower structures comprising fluorine exhibit superomniphobic properties. The surface energy corresponding to a superomniphobic surface can be increased by, for example, irradiating the surface with ultraviolet light. Irradiation removes fluorine as a function of irradiation time (FIG. 2a-b). Thus, the liquid repellent properties of the superomniphobic surface can be tuned to form areas of the surface that are omniphobic (i.e., less liquid repellent compared to superomniphobic), in other words, a surface having properties that make an area more liquid wettable than a superomniphobic surface.

The superomniphobic surface can also be divided into two or more domains, each domain having a different surface energy and each domain having a substantially uniform surface energy resulting from each domain receiving a different UV irradiation time to form the domains with surface properties ranging from superomniphobic to omniphobic.

The liquid repellent surface as described in this disclosure is not limited to any one chemical composition. Different chemical compositions that form liquid repellent surfaces can be arranged as a gradient of surface energy domains as for the methods described herein. The gradient of surface energy increases along one dimension in approximately an infinite number of small increments or in a finite number of larger increments. The width of each increment is defined as the longitudinal width of each domain, the dimension being in the direction of a traversing droplet that can be placed on the liquid repellent surface.

A liquid droplet that is placed at the top of a sloping liquid repellent surface will traverse the domains, for example, by rolling, sliding, or bouncing, when, for example, gravity compels the droplet to move from the domain with the lowest surface energy at the top of the slope and down the sloped liquid repellent surface until the droplet stops in a domain having a higher surface energy that cannot repel the droplet.

Tunable Superomniphobic Surfaces for Sorting Droplets by Surface Tension

The primary measure of wetting of a liquid on a non-textured (i.e., smooth) solid surface is the Young equilibrium (Philos. T. R. Soc. London, 1805, 65) contact angle θ. When the liquid droplet contacts a textured (i.e., rough) solid surface, it displays an apparent contact angle θ*, and it can adopt one of the following two configurations to minimize its overall free energy—the fully wetted Wenzel state (Ind. Eng. Chem., 1936, 28, 988) or the Cassie-Baxter state (T. Faraday Soc., 1944, 40, 0546). The Cassie-Baxter state is preferred in designing super-repellent surfaces because it leads to high θ* and low contact angle hysteresis Δθ*. A surface is considered superhydrophobic if it displays θ*>150° and Δθ*<10° with water, and superoleophobic if it displays θ*>150° and Δθ*<10° with low surface tension liquids. Superomniphobic surfaces are both superhydrophobic and superoleophobic. In contrast, a surface is omniphobic if θ*>90° for both water and low surface tension liquids. Typically, superhydrophobic and superomniphobic surfaces are fabricated by combining low solid surface energy (typically $\gamma_{sv}$<15 mN m$^{-1}$) materials and textured surfaces. Although superhydrophobic surfaces can be fabricated with a wide variety of textures, fabrication of superomniphobic surfaces requires a re-entrant texture (i.e., multivalued surface topography).

Liquid droplets roll off easily from super-repellent surfaces because of the low $\Delta\theta^*$. Based on a balance between work done by gravity (left hand side of Equation 1) and work expended due to adhesion (right side of Equation 1), the roll off angle (i.e., the minimum angle $\omega$ by which the surface must be tilted relative to the horizontal for a droplet to roll off) on a super-repellent surface is given as:

$$\rho g V \sin \omega \approx \gamma_{lv} D_{TCL}(\cos \theta^*_{rec} - \cos \theta^*_{adv}) \quad (Eq.1)$$

Here, $D_{TCL}$ is the width of solid-liquid-vapor contact line perpendicular to the rolling direction, $\theta^*_{adv}$ and $\theta^*_{rec}$ are the apparent advancing and receding contact angles, respectively, $\rho$ is the density of the liquid, g is acceleration due to gravity, and V is the volume of the liquid droplet. When a liquid droplet with roll off angle $\omega$ is placed on a super-repellent surface tilted relative to the horizontal at a tilt angle $\alpha$, the liquid droplet will roll off from the surface when $\omega<\alpha$ and the liquid droplet will remain adhered (i.e., not roll off and stick) to the surface when $\omega>\alpha$.

Consider droplets with different surface tension, but the same volume. Typically, in systems with no specific solid-liquid interactions, liquids with lower $\gamma_{lv}$ adhere more to a super-repellent surface (i.e., display higher $\omega$) and liquids with higher $\gamma_{lv}$ adhere less (i.e., display lower $\omega$). This is because of the higher $D_{TCL}$ and higher $\Delta\theta^*$ associated with low $\gamma_{lv}$ liquids. So, when a super-repellent surface with solid surface energy $\gamma_{sv}$ is tilted at an appropriate tilt angle $\alpha$, it may be anticipated that certain higher surface tension liquid droplets with $\omega<\alpha$ will roll off from the surface while other lower surface tension liquid droplets with $\omega>\alpha$ will remain adhered to the surface. Similarly, when a super-repellent surface with identical texture, but a slightly different solid surface energy $\gamma'_{sv}$ is tilted at the same tilt angle $\alpha$, it may be anticipated that a different set of higher surface tension liquid droplets with $\omega'<\alpha$ will roll off from the surface and another set of lower surface tension liquid droplets with $\omega'>\alpha$ will remain adhered to the surface.

If $\gamma_{sv}<\gamma'_{sv}$, then $\omega<\omega'$, i.e., at a fixed tilt angle $\alpha$, the super-repellent surface with lower solid surface energy will allow more liquids with lower surface tension to roll off from the surface compared to the one with higher solid surface energy. In this manner, different super-repellent surfaces with identical texture can be used to sort droplets into different sets—one set of higher surface tension liquids that freely roll past the surface and another set of lower surface tension liquids that are trapped on the surface and so on. If the super-repellent surfaces are superhydrophobic, they can be used to sort only a narrow range of high $\gamma_{lv}$ liquids. On the other hand, if the super-repellent surfaces are superomniphobic, they can be used to sort a wide range of liquids with both high $\gamma_{lv}$ and low $\gamma_{lv}$. Utilizing the principles discussed thus far, we fabricated a simple device with multiple precisely tailored $\gamma_{sv}$ domains of tunable superomniphobic surfaces to sort liquid droplets by their surface tension.

We synthesized our superomniphobic surfaces via hydrothermal synthesis of titanium dioxide ($TiO_2$) nanostructures and subsequent surface modification with a fluorinated silane. The etching time $t_{etch}$ in hydrothermal synthesis allowed us to tailor the morphology of the $TiO_2$ nanostructures and obtain the required re-entrant texture. Low etching time ($t_{etch}=2$ h) resulted in bead-like $TiO_2$ nanostructures (FIG. 1a). After this surface was fluorinated, it displayed relatively low contact angles and high contact angle hysteresis (FIG. 1d) with water ($\gamma_{lv}=72.1$ mN m$^{-1}$; a representative high $\gamma_{lv}$ liquid) and n-hexadecane ($\gamma_{lv}=27.5$ mN m$^{-1}$; a representative low $\gamma_{lv}$ liquid) indicating that the surface roughness is unsuitable to render it super-repellent. On this surface, both water and n-hexadecane are primarily in the Wenzel state. Slightly higher etching time ($t_{etch}=4$ h) resulted in predominantly bead-like $TiO_2$ nanostructures along with a few flower-like $TiO_2$ nanostructures (FIG. 1b). After this surface was fluorinated, it displayed very high contact angles and very low contact angle hysteresis with water (FIG. 1d) indicating that it is superhydrophobic. However, the surface displayed relatively lower contact angles and higher contact angle hysteresis with n-hexadecane indicating that it is not superoleophobic. This is because of insufficient re-entrant textured nanostructures on the surface. On this surface, water is in the Cassie-Baxter state and n-hexadecane is primarily in the Wenzel state.

Sufficiently high etching time ($t_{etch}\geq 6$ h) resulted in flower-like $TiO_2$ nanostructures (FIG. 1c). After this surface was fluorinated, it displayed very high contact angles and very low contact angle hysteresis with water and n-hexadecane (FIG. 1d) indicating that it is both superhydrophobic and superoleophobic, i.e., superomniphobic. The re-entrant texture of the flower-like $TiO_2$ nanostructures coupled with the low solid surface energy ($\gamma_{sv}=10$ mN m$^{-1}$) imparted by the fluorinated groups rendered our surfaces superomniphobic. On this surface, both water and n-hexadecane are in the Cassie-Baxter state. The superomniphobicity is further evident from a wide range of liquids beading up (FIG. 1e) and bouncing (FIG. 1f) on the surface due to their high contact angles and low contact angle hysteresis.

While a single surface with a fixed solid surface energy is sufficient to sort liquids into two sets—one with higher surface tension liquids that freely roll past the surface and another with lower surface tension liquids that are trapped on the surface—it cannot provide a finer sorting of liquids by their surface tension. In order to sort a wide range of liquids by their surface tension, we fabricated a simple device with multiple, discrete domains with identical texture, but different precisely tailored solid surface energy (FIG. 3a). The solid surface energy of each discrete domain was tuned to the desired value by controlling the UV irradiation time. The discrete domains were fabricated along the length of the device in the order of increasing solid surface energy.

The device was tilted relative to the horizontal at an angle $\alpha$ with the lowest solid surface energy domain at the top of the incline and the highest solid surface energy domain at the bottom of the incline. When a liquid droplet is introduced at the top of the incline, depending on its surface tension, it will freely roll past the domains where its roll off angle $\omega<\alpha$ and it will get trapped in the first domain where its roll off angle $\omega'>\alpha$. As an example, here we demonstrate sorting of five different ~5 µL liquid droplets by their surface tension—water ($\gamma_{lv}=72.1$ mN m$^{-1}$), water+10% ethanol ($\gamma_{lv}=53.4$ mN m$^{-1}$), water+20% ethanol ($\gamma_{lv}=43.7$ mN m$^{-1}$), water+30% ethanol ($\gamma_{lv}=37.2$ mN m$^{-1}$) and water+60% ethanol ($\gamma_{lv}=28.7$ mN m$^{-1}$)—using a device with four precisely tailored solid surface energy domains—domain 1 ($\gamma_{sv}=12$ mN m$^{-1}$, $t_{UV}=2$ min), domain 2 ($\gamma_{sv}=14$ mN m$^{-1}$, $t_{UV}=4$ min), domain 3 ($\gamma_{sv}=17$ mN m$^{-1}$, $t_{UV}=6$ min) and domain 4 ($\gamma_{sv}=24$ mN m$^{-1}$, $t_{UV}=8$ min). We used water-ethanol mixtures to demonstrate droplet sorting because this allows us to systematically tune the surface tension of liquid droplets over a wide range (28.7 mN/m to 72.1 mN/m). We estimated the roll off angles for 5 µL droplets of each of the five liquids in each of the four domains by measuring the apparent contact angles and using Equation 1.

Based on the estimated roll off angles (FIG. 3g), when the device is tilted at an angle $\alpha=15°$, droplets of water+60% ethanol should get trapped in domain 1; droplets of water+

30% ethanol should freely roll past domain 1, but get trapped in domain 2; droplets of water+20% ethanol should freely roll past domains 1 and 2, but get trapped in domain 3; droplets of water+10% ethanol should freely roll past domains 1, 2 and 3, but get trapped in domain 4; and droplets of water should freely roll past all domains. These predictions match reasonably well with the experiments (FIG. 3b-3f) indicating that our devices with discrete domains of precisely tailored solid surface energy and a predetermined tilt angle (based on estimated roll off angles) can, for the first time, sort liquid droplets by their surface tension. Our devices can be reused multiple times after completely drying the adhered liquid droplets from a previous experiment. Multiple times refers to at least 20 or 25 in our experience, and the surfaces can often be reused hundreds or thousands of times. In some embodiments, the surfaces many need to be rinsed, washed, or otherwise treated or refreshed after a certain number of uses or upon introduction of contaminants to the surface. After treatment the surfaces can then be reused multiple times.

A careful inspection of sorting droplets by surface tension using our devices (FIG. 3b-3f) indicates that the droplets of the same liquid (with same surface tension) adhere at slightly different locations (typically <10 mm from each other) within a discrete domain (with same surface energy). We attribute this to the small variation in droplet volume (±0.5 μL) that leads to different kinetic energies of the droplets as well as the small spatial variation in the surface roughness (±0.2 μm) that leads to different droplet mobility. We ensured that each discrete domain is long enough (~15 mm) so that the kinetic energy of the accelerating droplets is completely overcome by the work expended due to adhesion precisely in the first domain, where its roll off angle is higher than the tilt angle. In other words, when a liquid droplet is introduced at the top of the incline, depending on its surface tension, it will freely roll past the domains where its roll off angle is lower than the tilt angle and it will get trapped in the first domain, where its roll off angle is higher than the tilt angle.

Fuel Sensor Applications.

Numerous developing countries in Asia (e.g., India) and Africa (e.g., Nigeria) offer subsidized fuels such as kerosene to support lighting and cooking needs of the rural poor. However, the lower cost of kerosene compared to market-rate fuels results in fuel adulteration; ~40% of the kerosene sold in India frequently gets blended with gasoline and diesel. The misuse of kerosene is hard to detect because conventional detection technologies are time consuming, expensive and require large amounts of fuel sample. Consequently, there is a critical need to develop and deploy rapid, low-cost, easy-to-use sensors to detect fuel adulteration in-the-field, specifically in developing economies where fuel quality is a concern.

We developed a portable, low-cost and power-free sensor that can rapidly detect compositions of liquid blends by sensing their surface tension. Our sensor was fabricated using superomniphobic surfaces, which are extremely repellent to virtually any liquid—aqueous or organic, acid or base or solvent, polar or nonpolar, and Newtonian or non-Newtonian. Virtually any liquid can bead up, bounce, and easily roll off of superomniphobic surfaces (FIG. 7a-b). The mobility of a liquid droplet on a superomniphobic surface-based sensor is strongly dependent on the liquid surface tension, which in turn depends on the composition of the liquid blend. We demonstrated that the surface chemistry, and consequently the solid surface energy and contact angle hysteresis (i.e., the difference between the advancing [maximum] and receding [minimum] contact angles) of our superomniphobic surface-based sensors can be tuned systematically. This allowed us to systematically tune the mobility of droplets with different surface tensions on our superomniphobic surfaces. Leveraging this principle, we fabricated a simple sensor that, for the first time, sorted droplets by surface tension.

We discovered that the superomniphobic-based surface tension sensor (mentioned above) can be optimized to detect small differences in surface tension and consequently could detect adulteration of diesel blended with small amounts of kerosene (5, 10, and 20% blends); diesel and kerosene have slightly different surface tensions (diesel=27 mN m$^{-1}$, kerosene=23 mN m$^{-1}$). In this work, we develop and deploy rapid, field-deployable, low-cost sensors that are capable of detecting kerosene-adulterated fuel.

The core technology uses a superomniphobic surface to sense liquids with different surface tensions. We have studies using this technology to detect kerosene-adulterated diesel based on the differences in surface tension. Below, we describe the fabrication process used to create the superomniphobic surface and discuss findings from those initial studies.

Fabrication Process: We employed an extremely simple and scalable spray coating process (for example, using an airbrush) to fabricate the superomniphobic surface; this will allow us to create a truly low-cost sensor that can be mass produced. First, fumed silica particles were functionalized with a fluorinated silane to form a suspension of the fluorinated silica (F—SiO$_2$) particles in a certain solvent (e.g., acetone, chloroform, etc). Simultaneously, a solution of an adhesive (e.g., cyanoacrylate, polyurethane etc.) in the same solvent was prepared. Subsequently, the suspension of F—SiO$_2$ particles and the solution of the adhesive were mixed and spray coated onto a glass slide (FIG. 8a). The resulting surfaces were superomniphobic to pure diesel and kerosene. We used a scanning electron microscope (SEM) to assess the surface morphology and uniformity of the coating (FIG. 8b). The superomniphobicity of the surface was characterized by measuring the contacts angles and roll off angles of liquids with a wide range of surface tensions using a contact angle goniometer.

To fabricate the sensor, alternative materials with appropriate re-entrant texture such as paper, fabrics, textured metals (aluminum, zinc, copper, and stainless steel) and textured metal alloys, textured polymers and polymer composites can be used. Also, alternative surface chemistries with low surface energy such as fluorinated/alkyl silanes, fluorinated/alky thiols, fluorinated/alky monomers, fluorinated/alkyl phosphates, fluorinated/alkyl acids, and fluorinated/alkyl-POSS can also be used.

Detection of Fuel Adulteration: The mobility of a liquid droplet on a superomniphobic surface is strongly dependent on surface tension, which in turn depends on the composition of the liquid. Diesel and kerosene have slightly different surface tensions (diesel=27 mN m$^{-1}$, kerosene=23 mN m$^{-1}$). Our superomniphobic surface would allow us to detect small differences in the surface tensions of different blends of diesel and kerosene.

Figure 9:
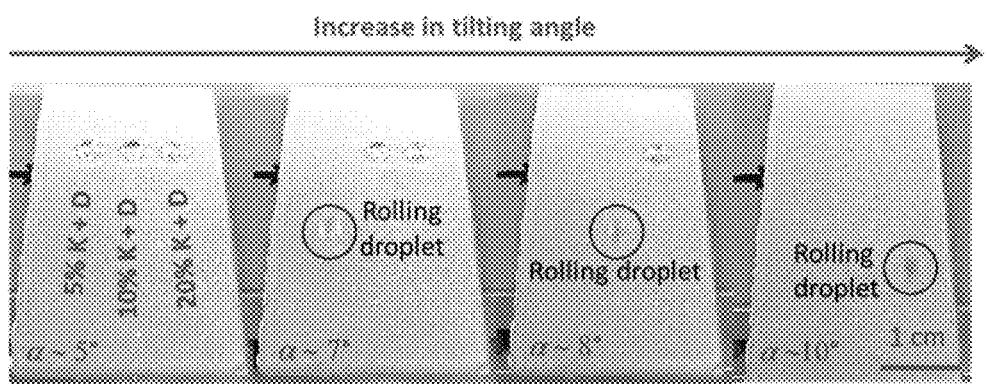
FIG. 9. A series of snapshots captured from the video showing the fuel quality sensor. Three droplets, diesel+5%, 10% and 20% kerosene, respectively from left to right are placed on a horizontal superomniphobic surface. The surface is then tilted gradually from 0 to 10 degrees.

In our experiments, we placed droplets of diesel+5% kerosene (high surface tension), diesel+10% kerosene (intermediate surface tension) and diesel+20% kerosene (low surface tension) blends on a horizontal superomniphobic surface. By gradually increasing the tilt angle (i.e., the angle by which the surface is tilted relative to the horizontal), we observed that the droplet of diesel+5% kerosene blend rolled off the superomniphobic surface first (while droplets of diesel+10% kerosene and diesel+20% kerosene blends remained adhered to the surface). As we increased the tilt angle further, the droplet of diesel+10/o kerosene blend rolled off (while the droplet of diesel+20% kerosene blend remained adhered to the surface). Finally, as we increased the tilt angle even further, the droplet of diesel+20% kerosene blend also rolled off. The results are described pictorially in FIG. 9. It is evident that the droplets of different diesel+kerosene blends rolled off in the order of decreasing surface tension. In other words, a lower surface tension liquid requires a higher tilt angle to roll off from the superomniphobic surface.

Figure 10:
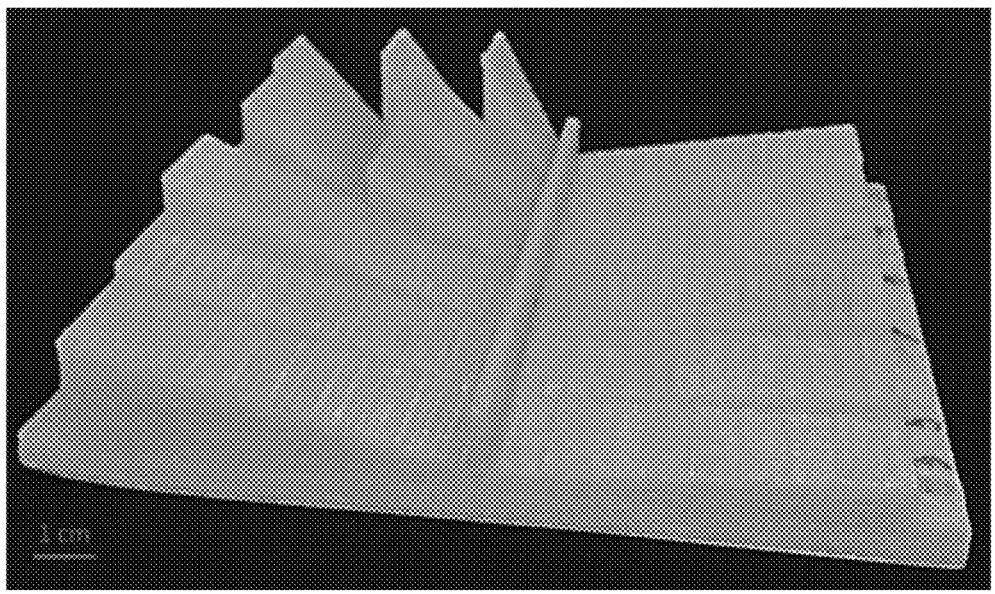
FIG. 10. An illustration of a field sensor with multiple angled sensing surfaces.

A Field-Deployable Sensor: Our superomniphobic surface enables the design, and development of a field-deployable sensor kit that can detect small levels of kerosene adulteration (<5%) and can be used by an untrained user (we expect the level of complexity to be akin to a litmus paper test). The parts of the sensor kit comprise four components: (1) an inexpensive machined plastic or wood block with four to six angled surfaces (for an example with multiple angled surfaces, see FIG. 10) that each hosts a superomniphobic coating on the angled surface (also referred to as the sensing surface), (2) an inexpensive tubular bubble level attached to the plastic/wood block to ensure that the sensor is placed on a horizontal surface (3) an inexpensive plastic transfer pipette to hold and deliver the fuel sample droplets onto the sensing surface and (4) a short field manual in multiple languages (for example, English, Hindi and Tamil). The kit's operation will require the operator to extract a small volume of fuel sample into a plastic pipette, which will then be used to deliver liquid droplets to the elevated end of the angled surfaces. As the propensity to roll off at a given tilt angle is dependent on the surface tension of the liquid (and indirectly on the level of adulteration), the observed 'roll offs' and lack of 'roll off' on the different angled surfaces will be used to assess the minimum and maximum level of kerosene adulteration. Additionally, the field sensors can be used repeatedly. With very few parts and the simple nature of the measurement paradigm, the sensor kit is anticipated to cost very little.

Current technologies to measure fuel adulteration are expensive, hard to implement and need to be performed offline by trained professionals. The primary strength of our technology is that it will allow us to build a rapid, field-deployable and low-cost sensor that can be operated by an untrained user. In the absence of an alternative technology, these three attributes are well suited for multiscale (i.e., from governments to individuals) applications.

In summary, we developed a low-cost and power-free sensor that can rapidly detect compositions of liquid blends by sensing their surface tension. Our sensor is fabricated using superomniphobic surfaces (i.e., surfaces that can repel virtually all liquids). Superomniphobic surfaces can be fabricated by combining a surface chemistry possessing a low solid surface energy (e.g., fluorocarbon or hydrocarbon chemistry) with an appropriate texture (e.g., nanoparticles). In this work, we fabricated superomniphobic surfaces by coating a substrate with a blend of an adhesive and fluorinated silica (F—$SiO_2$) particles. The tilt angle required for roll off provides a proxy measure for the surface tension of the liquid and a method to detect the level of kerosene adulteration in the fuel. Given the straightforward measurement paradigm based on the tilt angle our sensors can rapidly detect and quantify kerosene adulteration in gasoline and diesel fuels in-the-field. Results show high sensitivity can be achieved through our sensor even when there are small differences in surface tensions The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Fabrication of Devices with Discrete Solid Surface Energy Domains

Figure 5:
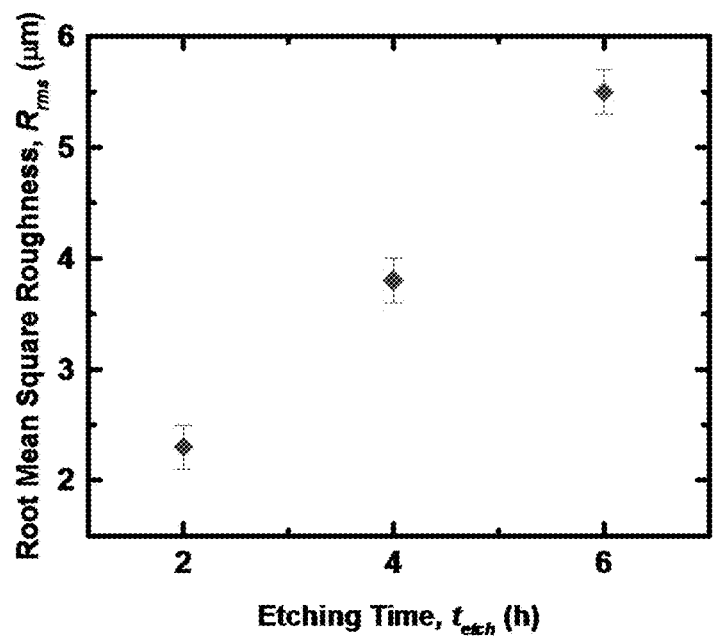
FIG. 5. The root mean square roughness of the surfaces at different etching times.

Hydrothermal Synthesis of Superomniphobic Surfaces: Titanium (Ti) sheets (6 cm long×2 cm wide×0.8 mm thick) were cleaned by sonication in acetone and isopropanol, dried with nitrogen and placed in a PTFE-lined stainless steel autoclave containing 20 mM hydrofluoric acid (Sigma Aldrich). The autoclave was sealed and the Ti sheets were etched under hydrothermal conditions at 100° C. for different times (FIG. 4). As the etching time $t_{etch}$ increased, more $TiO_2$ nanostructures formed and consequently the roughness $R_{rms}$ of the surface increased (FIG. 5). After hydrothermal synthesis, the samples were rinsed thoroughly with deionized water, dried with nitrogen, and the surface was modified via vapor phase silanization at 120° C. for 1 hour using 200 μL of heptadecafluoro-1,1,2,2-tetrahydrodecyl trichlorosilane (Gelest, Inc). Superomniphobic surfaces with flower-like $TiO_2$ nanostructures were obtained by etching under hydrothermal conditions for 6 h or longer.

Characterization of Surface Morphology: After hydrothermal synthesis, the surfaces were imaged using a scanning electron microscope (SEM) (JEOL JSM-6500F) at 15 kV to determine the surface morphology.

Characterization of Surface Roughness: After hydrothermal synthesis, the root mean square roughness $R_{rms}$ of the surfaces was measured using an optical profilometer (Zygo Zescope). At least three measurements were performed on each surface.

Tuning Surface Chemistry and Solid Surface Energy Via UV Irradiation: The surface chemistry, and consequently the solid surface energy, of the superomniphobic surfaces with flower-like $TiO_2$ nanostructures was tuned by UV irradiating the surface for different times using a 254 nm UV bench lamp (UVP XX-40S). The samples were placed about 2 cm away from the UV lamp.

Characterization of Surface Chemical Composition: X-ray photo-electron spectroscopy (XPS) analysis was conducted on the surfaces before and after UV irradiation using a PHI-5800 spectrometer (Physical Electronics) to verify the degradation of the fluorinated groups (—$CF_2$ and —$CF_3$) upon UV irradiation. XPS was conducted using a monochromatic Al—K X-ray source operated at 15 kV and photoelectrons were collected at a takeoff angle of ~45° relative to the sample surface.

Synthesis of Non-textured TiO$_2$ Surfaces to Determine Solid Surface Energy: Non-textured, uniform, thin films of TiO$_2$ (150 nm thick) were deposited on piranha cleaned glass substrates via RF ion beam sputtering with ion beam assist using a Ti target under 130 µTorr of oxygen in argon. Subsequently, the non-textured TiO$_2$ surfaces were modified via vapor phase silanization at 120° C. for 1 hour using 200 µL of heptadecafluoro-1,1,2,2-tetrahydrodecyl trichlorosilane. The advancing contact angles measured at different UV irradiation times on fluorinated, non-textured TiO$_2$ surfaces were used to estimate the solid surface energy with the Owens-Wendt approach (*J. Appl. Polym. Sci.*, 1969, 13, 1741). The error in solid surface energy was ±0.5 mN m$^{-1}$.

Measurement of Contact Angles and Roll Off Angles: The contact angles and roll-off angles were measured using a contact angle goniometer (Ramé-Hart 200-F1). The contact angles were measured by advancing or receding 5±0.5 µL droplets on the surface using a micrometer syringe (Gilmont). The roll-off angles were measured by tilting the stage until the 5±0.5 µL droplet rolled off from the surface. At least six measurements were performed on each surface. The errors in contact angle and roll-off angle were ±1° and ±0.5°, respectively.

Fabrication of the Devices with Discrete Solid Surface Energy Domains: Devices with discrete solid surface energy domains were fabricated by UV irradiating the desired area of a superomniphobic surface for the desired time while masking the other areas with a PTFE tape. In order to account for droplets of the same liquid (with same surface tension) adhering at slightly different locations (typically <10 mm from each other) within a discrete domain (due to small variations in droplet volume and surface roughness), we fabricated each discrete domain to be long enough (~15 mm) so that the kinetic energy of the accelerating droplets is completely overcome by the work expended due to adhesion precisely in the first domain where its roll off angle is higher than the tilt angle.

Fabrication of a Fuel Sensor: For fabrication of fuel sensor superomniphobic surfaces, 400 mg of fumed silica particles (diameter ~7 nm; Sigma Aldrich) were functionalized in a solution consisting of 20 mL n-hexane (Fisher) and 0.5 mL heptadecafluoro-1,1,2,2-tetrahydrodecyl trichlorosilane (Gelest) for three days to form a suspension of fluorinated silica (F—SiO$_2$) particles. 0.5 mL of an adhesive (e.g., Gorilla™ glue) was then spin coated on a glass slide. Immediately after spin coating glue, the suspension of F—SiO$_2$ particles was spray coated on the glue layer. Spray coating was done at a pressure of 30 psi using an air brush (Paasche) held 10 cm from the surface. The surface was then allowed to dry at room temperature for a day. The mobility of a liquid droplet on a superomniphobic surface is strongly dependent on the liquid surface tension, which in turn depends on the composition of the liquid blend. Our results indicate that our superomniphobic surface-based sensor can easily detect differences between diesel (27 mN/m), kerosene (23 mN/m) and various blends of diesel and kerosene (5%, 10%, and 20%).

Example 2

Estimation of Solid Surface Energy

Owens-Wendt approach was used to estimate the solid surface energy $\gamma_{sv}$ of the fluorinated TiO$_2$ surfaces before and after UV irradiation. n-hexadecane ($\gamma_{lv}$=27.5 mN m$^{-1}$) was used as the non-polar liquid to estimate the dispersive component of the solid surface energy $\gamma_{sv}^d$ and water ($\gamma_{lv}^d$=21.1 mN m$^{-1}$ and $\gamma_{lv}^p$=51.0 mN m$^{-1}$) was used as the polar liquid to estimate the polar component of the solid surface energy $\gamma_{sv}^p$. The advancing contact angle $\theta_{adv}$ is approximately equal to Young's contact angle, hence the advancing contact angles measured at different UV irradiation times $t_{UV}$ on fluorinated, non-textured TiO$_2$ surfaces were used to estimate the solid surface energy (Table 1).

TABLE 1

Advancing contact angles of water and n-hexadecane and solid surface energies, at different UV irradiation times, for fluorinated, non-textured TiO$_2$ surfaces.

| | $\theta_{adv}$ | | |
|---|---|---|---|
| $t_{UV}$ (min) | n-hexadecane | Water | $\gamma_{sv}$ (mN m$^{-1}$) |
| 0 | 80° | 120° | 10 |
| 2 | 77° | 108° | 12 |
| 4 | 73° | 104° | 14 |
| 6 | 69° | 97° | 17 |
| 8 | 62° | 85° | 24 |
| 10 | 56° | 74° | 31 |

Example 3

Apparent Contact Angles of Different Liquids on Superomniphobic Surfaces Before UV Irradiation The apparent advancing and the apparent receding contact angles of different liquids on superomniphobic surfaces before UV irradiation ($t_{UV}$=0 min) are listed in Table 2.

TABLE 2

The apparent advancing and the apparent receding contact angles of different liquids on superomniphobic surfaces before UV irradiation.

| Liquid | Surface tension (mN m$^{-1}$) | $\theta_{adv}$* | $\theta_{rec}$* |
|---|---|---|---|
| Water | 72.1 | 164° | 162° |
| Water + 10% Ethanol | 53.4 | 161° | 159° |
| Water + 20% Ethanol | 43.7 | 159° | 155° |
| Water + 30% Ethanol | 37.2 | 156° | 153° |
| Water + 60% Ethanol | 28.7 | 154° | 150° |
| n-hexadecane | 27.5 | 153° | 150° |

Example 4

Influence of UV Irradiation Time on Solid Surface Energy, and Apparent Contact Angles and Roll Off Angles of Water and n-Hexadecane The influence of $t_{UV}$ on $\gamma_{sv}$ and consequently on the apparent advancing and receding contact angles $\theta^*_{adv}$ and $\theta^*_{rec}$ and roll off angles ω of water and n-hexadecane on our superomniphobic TiO$_2$ surfaces (i.e., fluorinated surfaces with flower-like TiO$_2$ nanostructures) is shown in Table 3. It is evident from Table 3 (and FIG. 2*f*) that $\theta^*_{adv}$ and $\theta^*_{rec}$ decrease for both n-hexadecane and water with increasing $t_{UV}$. Further, it is evident that $\theta^*_{rec}$ decreases (see FIG. 2*f*) and ω increases (see FIG. 2*g*) more rapidly for n-hexadecane (lower $\gamma_{lv}$ liquid) compared to water (higher $\gamma_{lv}$ liquid) with increasing $t_{UV}$. In this work, our primary interest lies in $t_{UV}$≤10 min because at $t_{UV}$≥10 min, n-hexadecane droplets remain adhered and can no longer roll off, i.e., the mobility of n-hexadecane droplets can no longer be tuned or changed. For longer UV irradiation times (i.e., 10 min<$t_{UV}$<30 min), our experiments indicate that the apparent receding contact angles of n-hexadecane continue to decrease more rapidly than water. For very long UV irradiation times (i.e., $t_{UV}$>30 min), our experiments indicate that the surfaces become superomniphilic (i.e., the apparent contact angles of both water and n-hexadecane are ~0°).

TABLE 3

The apparent advancing and receding contact angles and roll off angles of water and n-hexadecane on superomniphobic surfaces after UV irradiation.

| $t_{UV}$ (min) | $\gamma_{sv}$ (mN m$^{-1}$) | $\theta_{adv}^*$ n-hexa-decane | $\theta_{adv}^*$ Water | $\theta_{rec}^*$ n-hexa-decane | $\theta_{rec}^*$ Water | $\omega$ n-hexa-decane | $\omega$ Water |
|---|---|---|---|---|---|---|---|
| 0 | 10 | 153° | 164° | 150° | 162° | 5° | 2° |
| 2 | 12 | 144° | 162° | 125° | 155° | 16° | 3.5° |
| 4 | 14 | 139° | 158° | 114° | 151° | 27° | 5° |
| 6 | 17 | 131° | 155° | 102° | 147° | 44° | 7° |
| 8 | 24 | 124° | 151° | 89° | 141° | 68° | 11° |
| 10 | 31 | 120° | 144° | 70° | 134° | No roll off | 13° |

Example 5

Estimation of Roll Off Angles

Based on a balance between work done by gravitational force and work expended due to adhesion, the roll off angle $\omega$ on a super-repellent surface is given as:

$$\rho g V \sin \omega \approx \gamma_{lv} D_{TCL}(\cos \theta^*_{rec} - \cos \theta^*_{adv}) \quad \text{(Eq. 2)}$$

Here, $\gamma_{lv}$, $\rho$ and V are surface tension, density and volume of the liquid droplet, respectively, and g is the gravitational acceleration. $\theta^*_{adv}$ and $\theta^*_{rec}$ are the apparent advancing contact angle and the apparent receding contact angle, respectively. $D_{TCL}$ is the width of the triple phase contact line perpendicular to the rolling direction. When the shape of the droplet does not deviate significantly from a spherical cap, the width of the triple phase contact line can be computed as:

$$D_{TCL} = 2\cos\left(\overline{\theta}^* - \frac{\pi}{2}\right)\left[\frac{3V}{\pi(2 - 3\cos\overline{\theta}^* + \cos^3\overline{\theta}^*)}\right]^{\frac{1}{3}} \quad \text{(Eq. 3)}$$

Here, $\overline{\theta}^*$ is the average apparent contact angle, given as:

$$\cos\overline{\theta}^* = \frac{\cos\theta^*_{adv} + \cos\theta^*_{rec}}{2} \quad \text{(Eq. 4)}$$

The estimated roll off angles of different liquids shown in FIG. 2g and FIG. 3g were obtained using Equations 2-4.

Example 6

Roll Off Angles of Water-ethanol Mixtures

The estimated roll off angles of different water-ethanol mixtures in each of the discrete domains of our device are listed in Table 4 (see FIG. 3g).

TABLE 4

Apparent advancing and apparent receding contact angles, and the estimated roll off angles of different water-ethanol mixtures in each of the discrete domains shown in FIGS. 3b-3f.

| | | Water | Water + 10% Ethanol | Water + 20% Ethanol | Water + 30% Ethanol | Water + 60% Ethanol |
|---|---|---|---|---|---|---|
| Surface tension (mN m$^{-1}$) | | 72.1 | 53.4 | 43.7 | 37.2 | 28.7 |
| Domain 1 | $\theta_{adv}^*$ | 162° | 158° | 156° | 150° | 145° |
| ($t_{UV}$ = 2 min; | $\theta_{rec}^*$ | 155° | 150° | 147° | 141° | 121° |
| $\gamma_{sv}$ = 12 mN m$^{-1}$) | $\omega$ | 3° | 3° | 4° | 5° | 17° |
| Domain 2 | $\theta_{adv}^*$ | 158° | 152° | 146° | 141° | 140° |
| ($t_{UV}$ = 4 min; | $\theta_{rec}^*$ | 151° | 140° | 132° | 117° | 111° |
| $\gamma_{sv}$ = 14 mN m$^{-1}$) | $\omega$ | 4° | 8° | 11° | 24° | 27° |
| Domain 3 | $\theta_{adv}^*$ | 155° | 143° | 140° | 132° | 131° |
| ($t_{UV}$ = 6 min; | $\theta_{rec}^*$ | 147° | 132° | 109° | 101° | 95° |
| $\gamma_{sv}$ = 17 mN m$^{-1}$) | $\omega$ | 6° | 11° | 44° | 46° | 47° |
| Domain 4 | $\theta_{adv}^*$ | 151° | 129° | 127° | 126° | 122° |
| ($t_{UV}$ = 8 min; | $\theta_{rec}^*$ | 141° | 115° | 95° | 90° | 81° |
| $\gamma_{sv}$ = 24 mN m$^{-1}$) | $\omega$ | 9° | 24° | 74° | 82° | 84° |

It is evident from Table 4 that all of our UV irradiated surfaces used to fabricate the device have finite roll off angles ($\omega$<90°) with the liquids listed. While these liquid droplets may adhere to a UV irradiated surface at low tilt angles ($\alpha$<$\omega$), they roll off from the UV irradiated surface at higher tilt angles ($\alpha$>$\omega$). If the droplets were completely in the Wenzel state, they would remain adhered to the surface and no longer exhibit mobility (i.e., droplets would not have a finite roll off angle $\omega$). Based on this, we conclude that the droplets on the UV irradiated surfaces used to fabricate the device (see FIGS. 3b-3f) are primarily in the Cassie-Baxter state.

Further, it is evident from Table 4 that the contact angle hysteresis of droplets with lower surface tension is higher than that of droplets with higher surface tension. Contact angle hysteresis primarily arises from surface roughness and heterogeneity. It is related to the energy barriers that a liquid droplet must overcome during its movement along a solid surface, and thus characterizes the resistance to droplet movement. Typically, the resistance to droplet movement is higher for lower surface tension liquids compared to higher surface tension liquids. This is possibly because lower surface tension liquids have higher solid-liquid contact area (and longer triple phase contact line), which in turn is due to their lower contact angles. Consequently, on our tunable superomniphobic surfaces, for any given solid surface energy, the contact angle hysteresis of droplets with lower surface tension is higher than that of droplets with higher surface tension.

Example 7

Reusability of Our Devices

Figure 6:
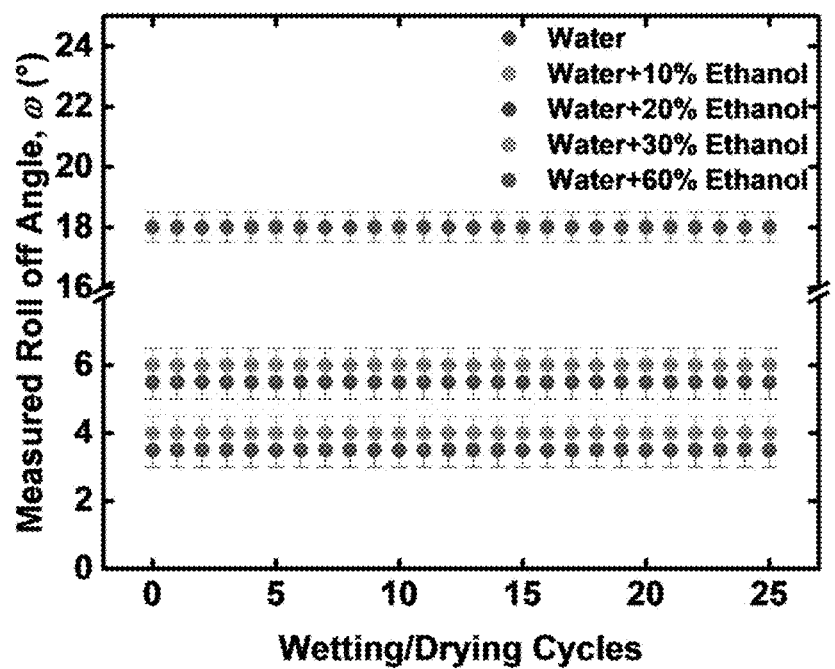
FIG. 6. The measured roll off angles of different liquids on the domain with $\gamma_{sv}$=12 mN m$^{-1}$ after wetting with ethanol and subsequently drying, for 25 times.

In order to evaluate the reusability of our devices, we first wet each discrete solid surface energy domain with an extremely low surface tension liquid (e.g., ethanol; $\gamma_{lv}$=22.1 mN m$^{-1}$) that remained adhered to the surface. Then, we completely dried the liquid on the surface by heating. Subsequently, we measured the roll off angles of different liquids in each domain to verify that the surface repellence has not been altered. Our experiments indicated that the roll off angles of different liquids in each domain remained unaltered even after a few wetting/drying cycles. To illustrate this with an example, here we present (FIG. 6) the measured roll off angles of different liquids (water, water+10% ethanol, water+20% ethanol, water+30% ethanol, and water+60% ethanol) on one of the domains with $\gamma_{sv}$=12 mN m$^{-1}$ after wetting with ethanol and subsequently drying for 25 times. The functionality of the device remains un-altered up to 25 cycles. As we increase the number of cycles further, the range over which we can sort droplets by surface tension decreases. This is because the re-entrant texture of our superomniphobic surfaces starts to deteriorate with increased cycles. This in turn causes the low surface tension liquid droplets to adopt the Wenzel state (and consequently, the droplet mobility can no longer be tuned) at increasingly more locations on the surface.

SUMMARY

In summary, we synthesized superomniphobic surfaces with fluorinated, flower-like TiO$_2$ nanostructures. We demonstrate that the surface chemistry, and consequently the solid surface energy, of our superomniphobic surfaces can be tuned using UV irradiation. This allows us to systematically tune the mobility of droplets with different surface tensions on our superomniphobic surfaces. Leveraging the selective mobility of droplets on our superomniphobic surfaces based on their surface tensions, we fabricated a simple device with precisely tailored solid surface energy domains that, for the first time, can sort droplets by surface tension ($\gamma_{lv}$=28.7 mN/m to 72.1 mN/m). Our devices can be fabricated easily in a short time and each device can be reused multiple times to sort droplets by surface tension. In addition, using estimated roll off angles, new devices can be systematically designed with predetermined tilt angle, number and surface energy of superomniphobic domains to sort droplets with different surface tension ranges and different droplet volumes. Our methodology and mechanism are applicable to a wide range of surface tensions and droplet volumes as long as the droplets are in the Cassie-Baxter state and not all in the Wenzel state. We envision that our methodology for droplet sorting will enable inexpensive and energy-efficient analytical devices for personalized point-of-care diagnostic platforms, lab-on-a-chip systems, biochemical assays and biosensors.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An apparatus for analyzing a property of a liquid, the apparatus comprising:
   a surface comprising superomniphobic and omniphobic areas, the surface having a first end and a distal end, and a gradient of two or more domains, each domain occupying different positions on the surface, wherein the superomniphobic and omniphobic areas comprise TiO$_2$ nano-flower three-dimensional structures that establish a re-entrant texture on the surface,
   wherein a first domain is at the first end and each other domain has an increased surface energy relative to the domain immediately preceding it; and
   wherein when a liquid droplet is placed on the first domain, having the lowest surface energy, and the surface is inclined relative to horizontal, the droplet traverses part or all of one or more of the domains and the domain where the droplet comes to the rest is indicative of the surface tension of the liquid.

2. The apparatus of claim 1 wherein the first end is at the top of an incline having a slope toward the distal end.

3. The apparatus of claim 1 wherein the longitudinal width of each domain is about 0.5 mm to about 10 cm.

4. The apparatus of claim 1 wherein the TiO$_2$ structures are surface modified with a fluoroalkyl silane.

5. An apparatus for comprising:
   a titanium metal sheet having a first end and a distal end, and a layer of a TiO$_2$ nano-flower three-dimensional structure having a re-entrant surface texture wherein the TiO$_2$ is surface modified with a fluoroalkyl silane and the surface modified TiO$_2$ nano-flower structures form a superomniphobic surface on the sheet; and
   the surface comprises a gradient of two or more domains from the first end to the distal end; wherein
   the domains occupy different positions on the sheet and are ordered in increasing surface energy, the first end of the sheet having the lowest surface energy, the distal end of the sheet having the highest surface energy, and each of the second or more domains have increased surface energy relative to the domain immediately preceding it;
   the first domain comprises the superomniphobic surface and each of the second or more domains comprise omniphobic areas having less than superomniphobicity; and
   the width of each domain is about 0.1 cm to about 10 cm.

6. The apparatus of claim 5 wherein when a liquid droplet is placed at the first end closest to the lowest surface energy domain of the gradient and the surface is inclined relative to horizontal, the droplet traverses part or all of one or more of the domains and the domain where the droplet comes to the rest is indicative of the surface tension of the liquid.

7. The apparatus of claim 6 wherein the difference in surface energy between each adjacent domain is less than about 20 mN/m, and the difference in surface energy between at least two or more adjacent domains is less than 10 mN/m.

8. A method for analyzing a property of a liquid, the method comprising:
   a) placing a liquid droplet on an apparatus comprising:
      i) a surface comprising superomniphobic and omniphobic areas, the surface having a first end and a distal end, the first end at the top of an incline and having a slope toward the distal end; and
      ii) the surface comprises a gradient of two or more domains, each domain occupying different positions on the surface, wherein the first domain, having the lowest surface energy, is closest to the first end and each of the second or more domains have an increased surface energy relative to the domain immediately preceding it;
      wherein when the droplet is placed at the first end, the droplet traverses part or all of one or more of the domains; and
   b) determining the final position of the droplet;
wherein the domain where the droplet comes to the rest is indicative of the surface tension of the liquid.

9. The method of claim 8 wherein when the roll off angle of the droplet is lower than the tilt angle of the incline of a particular domain, the droplet rolls off the domain, and if the roll off angle is higher than the tilt angle of the incline of a particular domain, the droplet remains on the domain.

10. The method of claim 8 wherein the superomniphobic and omniphobic areas comprise $TiO_2$ nano-flower three-dimensional structures that establish a re-entrant texture on the surface, wherein the $TiO_2$ structures are surface modified with a fluoroalkyl silane.

11. The method of claim 8 wherein each of the second or more domains surfaces have been modified with, for example, ultraviolet irradiation, plasma, or chemicals, to increase the surface energy of the domains, wherein increasing the surface modification provides a domain having increased surface energy.

12. The method of claim 8 wherein the difference in surface energy between each adjacent domain is less than about 20 mN/m.

13. The method of claim 8 wherein the volume of the droplet is about 0.1 µL to about 200 µL.

14. The method of claim 8 wherein the diameter of the droplet is about 0.1 mm to about 4 mm.

15. The method of claim 8 wherein the liquid is a pure compound or the liquid comprises a mixture of two or more components, wherein liquids of different compositions achieve different final positions, thereby indicating their different compositions relative to each other.

16. The method of claim 8 wherein the droplet comprises aqueous ethanol, a fuel mixture, a mixture of gasoline and kerosene, a mixture of diesel and kerosene, diesel, gasoline, biofluids, blood, or urine.

17. The method of claim 8 wherein the apparatus comprises two to about 100 domains.

18. The method of claim 8 wherein the surface energy of each one of the domains has been tuned by irradiating the domain with a 254 nm ultraviolet lamp wherein the distance between the ultraviolet lamp and the domain is about 2 cm and the irradiation time is from 10 seconds to 60 minutes.

19. The method of claim 18 wherein the irradiation is carried out for 10 seconds to 10 minutes.

20. The method of claim 8 wherein the incline has a tilt angle of about 0.5° to about 75°, relative to horizontal.

21. The method of claim 20 wherein the tilt angle is about 15°.

22. The method of claim 8 wherein the method is carried out with two or more droplets, optionally with different compositions, the method further comprising sorting each droplet by its final position where the final position is indicative of each droplet's composition or indicative of each droplet's surface tension.

23. The method of claim 22 wherein the apparatus comprises two or more surfaces at different angles.

24. A method for analyzing a property of a liquid, the method comprising:
   a) placing one or more liquid droplets on an apparatus comprising:
      one or more individual surfaces comprising superomniphobic and omniphobic areas, each surface having a first end and a distal end, the first end of each individual surface at the top of an incline and having a slope toward the distal end;
      wherein each of two or more individual surfaces have a different surface energy and a different tilt angle, or each of two or more individual surfaces have about the same surface energy and a different tilt angle,
      wherein
         when the droplet is placed at the first end of a surface, the droplet traverses part or all of one or more of the domains of the surface; or
         when the droplet is placed at the first end of a surface, the droplet traverses part or all of one individual surface having a fixed surface energy wherein the tilt angle is changed after each individual droplet is placed at the first end and traverses part or all of one individual surface; and
   b) determining the final position of the droplet;
wherein the domain where the droplet comes to the rest is indicative of the surface tension of the liquid.

25. The method of claim 24 wherein the superomniphobic and omniphobic areas comprise $TiO_2$ nano-flower three-dimensional structures that establish a re-entrant texture on the surface wherein the $TiO_2$ structures are surface modified with a fluoroalkyl silane.

26. The method of claim 24 wherein the surface energy of one or more of each individual surface has been tuned by irradiating at ultraviolet wavelengths for about 10 seconds to about 60 minutes.

27. The method of claim 24 wherein the incline has a tilt angle of about 0.5° to about 75°.

28. The method of claim 24 wherein the final position of each droplet is indicative of the droplet's composition or indicative of the droplet's surface tension.

29. The method of claim 24 wherein the droplet comprises aqueous ethanol, a hydrocarbon fuel, or a biofluid.

* * * * *